United States Patent [19]

Hechenbleikner

[11] 4,111,901
[45] Sep. 5, 1978

[54] HINDERED FIVE-MEMBERED NITROGEN RINGS AS POLYOLEFIN STABILIZERS

[75] Inventor: Ingenuin Hechenbleikner, West Cornwall, Conn.

[73] Assignee: Borg-Warner Corporation, Chicago, Ill.

[21] Appl. No.: 803,719

[22] Filed: Jun. 6, 1977

[51] Int. Cl.² ............................................. C08K 5/34
[52] U.S. Cl. ........................... 260/45.8 N; 260/23 H; 260/45.85 B; 260/326.2; 260/326.25
[58] Field of Search ..................... 260/45.8 N, 326.25, 260/326.2

[56] References Cited

U.S. PATENT DOCUMENTS

| 3,205,083 | 9/1965 | Green | 260/45.8 N |
| 3,325,445 | 6/1967 | Harris et al. | 260/45.8 N |
| 3,478,053 | 11/1969 | Szmuszkovicz | 260/45.8 N |
| 3,645,965 | 2/1972 | Murayama et al. | 260/45.8 N |
| 3,840,494 | 10/1974 | Murayama et al. | 260/45.8 N |
| 3,971,757 | 7/1976 | Rasberger | 260/45.8 N |
| 3,976,658 | 8/1976 | Avar et al. | 260/45.8 N |

Primary Examiner—Donald E. Czaja
Assistant Examiner—R. A. White
Attorney, Agent, or Firm—Joseph Shekleton

[57] ABSTRACT

Olefin polymers stabilized against deterioration caused by exposure to ultraviolet radiation. The stabilization is effected by means of an additive which is a hindered five-membered nitrogen ring. The five-membered ring is a substituted pyrrolidine or pyrroline having ester or amide groups. The compounds are characterized by excellent hydrolytic stability.

11 Claims, No Drawings

HINDERED FIVE-MEMBERED NITROGEN RINGS AS POLYOLEFIN STABILIZERS

This invention relates to the stabilization of polymers. More particularly it relates to the stabilization of olefin polymers against the deteriorating influence of ultraviolet radiation.

Ultraviolet light has a degradative effect on olefin polymers, the severity of which is dependent on the particular polymer and the geographical location of exposure. The degradation may take the form of discoloration, loss of tensile and impact strength, distortion of initial flexibility, dimensional change, surface craze, cracking, powdering or increased electrical conductivity. All of these effects may result from the breaking of carbon-to-carbon bonds in the polymer chain followed by immediate oxidation of the chain fragments.

It is well known that the addition of certain materials to an olefin polymer will impart a degree of stabilization to that polymer with respect to its resistance to the destructive forces of ultraviolet radiation. These materials, in one instance, function as preferential acceptors of incident ultraviolet radiation because they have a much higher affinity for such radiation than does the olefin polymer. It appears that they absorb harmful radiation and dissipate it as harmless energy. They thus form a protective shield for the polymer in which they are present.

U.S. Pat. No. 3,640,928 (Murayama et al.) shows the stabilization of synthetic polymers by the presence therein of certain piperidine compounds wherein the two carbon atoms adjacent to the ring nitrogen each contain two alkyl substituents. The piperidine compounds contain also an oxy substituent in the four-position and, in many instances, two or more piperidine nuclei are joined to one another by means of polyfunctional ether, ester, carbamate, sulfonate, etc. groups.

The stabilized polymer compositions of the present invention comprise olefin polymers stabilized against deterioration due to ultraviolet light and heat by the presence therein of a minor proportion, sufficient to provide such stabilization, of a five-membered nitrogen ring compound having the structure AOCOR, ACOOR or ACONHR' where A is a 2,2,5,5-tetraalkyl pyrrolidine or pyrroline wherein the alkyl groups are lower alkyl, R is alkyl or alkCOOA wherein alk is alkylene, and R' is alkyl or alkNHCO; or a salt thereof; It will be seen that the five-membered ring compounds are pyrrolines or pyrrolidines. These pyrrolines and pyrrolidines are characterized by unusual stability to hydrolysis, an important property in the stabilization of polymers.

The olefin polymers contemplated herein include homopolymers and copolymers of monoolefins, preferably those monoolefins containing 1–4 carbon atoms. Illustrative examples include polyethylene (both low and high density), polypropylene, polyisobutylene, and copolymers of ethylene, propylene and isobutylene. EPDM polymers are also contemplated. Polypropylene is preferred.

The alkyl groups on the carbon atoms alpha to the amine group in the above pyrrolidine or pyrroline compounds are lower alkyl groups, i.e., alkyl of 1–4 carbon atoms. Largely because of their ease of preparation those pyrrolidines and pyrrolines are preferred where these alkyl groups are all methyl. Otherwise, though, they may be the same or different methyl, ethyl, propyl and butyl groups.

The alkylene groups in these structures may be straight or branched chain and may contain 2 to 10 carbon atoms. Specific illustrative embodiments include ethylene, trimethylene, tetramethylene, hexamethylene, octamethylene, and decamethylene; propylene, 2-methyltrimethylene, 2-methyltetramethylene, 3-ethylpentamethylene, 2,4-dimethylhexamethylene and 3,5-dimethyloctamethylene.

Similarly, R and R' are alkyl groups of 1–17 carbon atoms, e.g., methyl, ethyl, propyl, hexyl, decyl, tridecyl, pentadecyl and heptadecyl.

A is as indicated either a 2,2,5,5-tetraalkyl pyrrolidine or pyrroline.

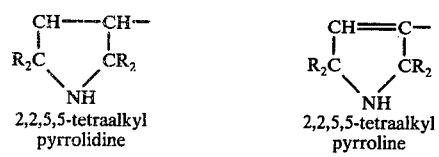

2,2,5,5-tetraalkyl pyrrolidine 2,2,5,5-tetraalkyl pyrroline where the R's are lower alkyl groups as above, i.e., having 1–4 carbon atoms.

Salts of the above substituted pyrrolidines and pyrrolines are also contemplated. These include both inorganic and organic salts including phosphates, carbonates, citrates, benzoates and aliphatic carboxylates having 10–20 carbon atoms.

The substituted pyrrolidines and pyrrolines herein may be prepared by known methods, as illustrated in the examples. Certain of these methods are taught in "Free Nitroxyl Radicals" by E. G. Rozantser, Plenum Press (1970).

The amount of substituted pyrrolidine or pyrroline which should be used in the polyolefins of this invention may vary widely depending upon the type, properties and particular uses of the polyolefin to be stabilized. In general they are added to the polyolefins so as to provide a concentration of from about 0.01% to about 5.0% based on the weight of polyolefin, preferably from about 0.05% to about 2.0%. They may be used as above, i.e., as the only additive in the polymer, but generally they will be used in combination with one or more other additives.

Other such additives include metal soaps such as calcium, zinc, barium, cadmium, tin, magnesium and aluminum soaps, i.e., polyvalent metal salts of fatty acids. These coact with the substituted pyrrolidines and pyrrolines herein to impart improved clarity to polyolefins upon prolonged exposure to atmospheric conditions. They also provide improved heat stability. They should be used in concentrations of from about 0.05% to about 3.0%, based on the weight of polyolefin.

Phenolic antioxidants may also be used in combination with the nitrogen compounds of this invention. Those phenolic antioxidants embraced by the structural formula

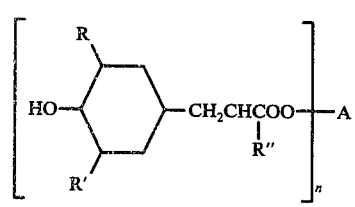

where R and R' are lower alkyl, i.e., alkyl of 1–10 carbon atoms, R'' is lower alkyl or hydrogen, n is 1–4, and A is the residue of an alkanol or alkane polyol, are preferred. Illustrative examples of A include

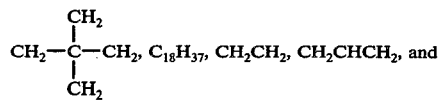

 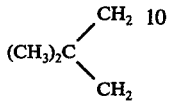

A contains 2–24 carbon atoms. Preferably, A is $C_{18}H_{37}$. The relative proportions of antioxidant used in the stabilized polyolefins of this invention range from about 0.01% to about 3.0%, based on polyolefin.

Other additives contemplated herein include phosphites, fillers, pigments, antistatic agents, etc.

As indicated, the five-membered nitrogen compounds of this invention are characterized not only by their property of stabilizing olefin polymers with respect to deterioration caused by ultraviolet radiation, but also by marked resistance to hydrolysis. The product of the procedure of Example 4, for example, remains unchanged when present for 218 hours as a 1% solution at 44° C. in a 90/10 mixture of tetrahydrofuran and water containing 0.42% of 0.05 molar hydrochloric acid. A compound of somewhat similar structure, i.e.,

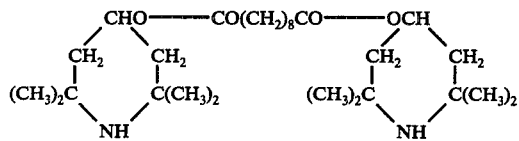

is decomposed by such treatment. It will be noted that the above compound, which is less stable to hydrolysis than the product of Example 4 herein, contains six-membered nitrogen rings rather than the five-membered nitrogen rings of the invention.

Preparation of the substituted pyrrolidines and pyrrolines herein is illustrated by the following examples.

EXAMPLE 1

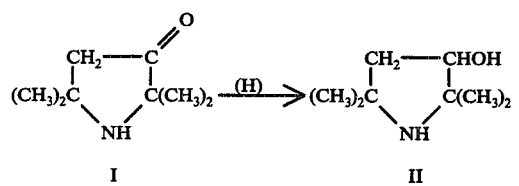

To a stirred mixture of 69.5 ml. of $NaAlH_2(OCH_2CH_2OCH_3)_2$ and 200 ml. of benzene, under nitrogen, there is added portionwise over a period of 15 minutes 16 g. (0.113 mol) of I dissolved in 150 ml. of benzene. The exothermic nature of the resulting reaction causes the temperature to rise to about 40° C. Stirring under nitrogen is continued for an additional four hours whereupon 50 ml. of water is added, causing the precipitation of a white pasty solid. The benzene solution is decanted from this solid, the solid extracted with two 50 ml. portions of benzene and these benzene extracts combined with the decanted benzene above, the whole is then filtered and concentrated by heating to a final temperature of 110° C./20 mm. The residue is a white crystalline solid (II).

EXAMPLE 2

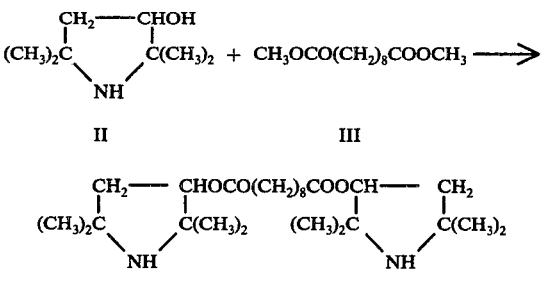

A mixture of 15 g. (0.105 mol) of II, 12 g. (0.052 mol) of III, 35 ml. of methanol and 0.1 g. of sodium methoxide is heated with stirring, under nitrogen, to remove the methanol over a period of 2.5 hours. The temperature is raised and kept at 150° C., still under nitrogen, for an additional 2.5 hours, then at 170° C. for 2.0 hours. The reaction product is dissolved in 50 ml. of benzene, washed with dilute aqueous sodium carbonate, then distilled. A fraction weighing 8 g. and boiling at 140°–185° C./0.2 mm. is taken as the desired diester (IV).

EXAMPLE 3

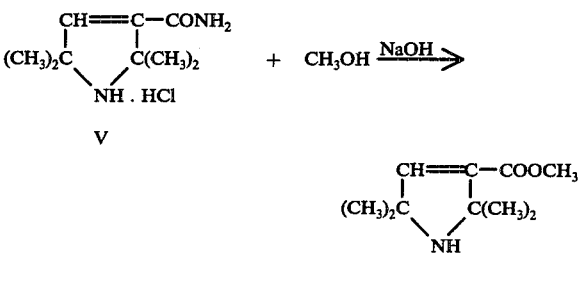

A mixture of 100 ml. of dry methanol and 29 g. (0.142 mol) of V is stirred while dry hydrogen chloride is bubbled through for 45 minutes. The temperature of the exothermic reaction is maintained at slightly below 50° C. by means of external cooling and the hydrogen chloride flow rate. Thereafter, the mixture is heated at reflux temperature for 8.5 hours during the first 1.5 hours of which time the introduction of dry hydrogen chloride is continued, although at a lesser rate. The product mixture on cooling deposits a white solid (ammonium chloride) which is removed by filtration. The filtrate, containing the hydrochloride of the desired methyl ester, is evaporated to dryness. The solid residue is washed with aqueous sodium hydroxide (a slight excess over that calculated to liberate the ester), and the mixture is extracted with toluene and fractionated to yield 11 g. of a fraction (VI), b.p. 70° C./5.5 mm.; $n_D^{25}$ 1.4570.

EXAMPLE 4

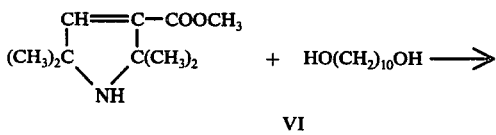

VI

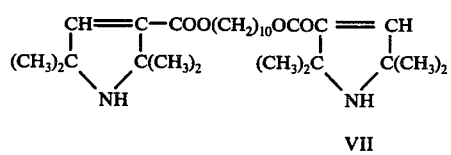

VII

A mixture of 7.65 g. (0.044 mol) of decamethylene glycol, a solution of 0.1 g. of sodium methylate in 8 ml. of methanol, and 17 g. (0.093 mol) of VI is heated briefly at 150° C./10 mm., so as to permit volatile matter, i.e., methanol, to escape. An infrared spectrum of the residue shows the absence of hydroxyl groups. It is dissolved in 50 ml. of benzene, filtered through charcoal and concentrated by heating to a final temperature of 110° C./10 mm. The residue, weighing 18 g., is a solid melting at 60°–64° C.

EXAMPLE 5

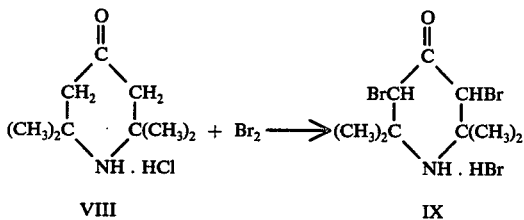

VIII                IX

To a solution of 50 g. (0.11 mol) of VIII dissolved in 110 ml. of acetic acid, at 10°–20° C., there is added portionwise over a period of two hours a solution of 68 g. (0.43 mol) of bromine in 50 ml. of acetic acid. The resulting mixture is stirred for an additional 2 hours then filtered and air-dried. M.P., 198°–200° C. (decomp.).

EXAMPLE 6

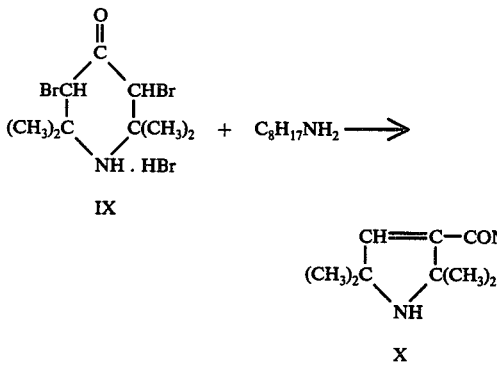

To a stirred solution of 58 g. (0.45 mol) of tert-octylamine, 75 ml. of dioxane and 50 ml. of water, at 10°–20° C., there is added 25 g. (0.06 mol) of IX over a period of 25 minutes. Stirring is continued for 3 hours while the temperature is permitted to rise to 25° C. The mixture then is poured into 150 ml. of 6% aqueous sodium hydroxide whereupon an oily layer separates and is isolated as the desired product (X). The aqueous layer is extracted with benzene and the benzene extract combined with the product layer and distilled. A fraction weighing 14.5 g. is collected at 125° C./0.1 mm. It solidifies on standing, M.P., 64°–66° C.

EXAMPLE 7

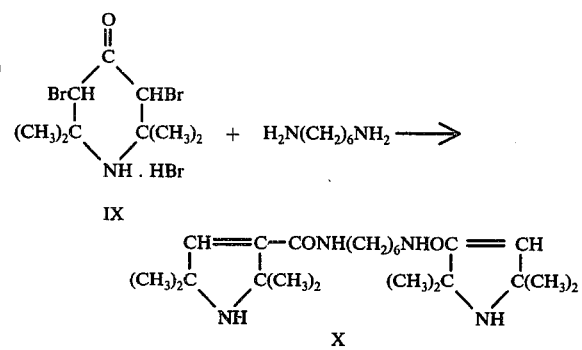

IX

X

To a stirred mixture of 2.2 g. (0.02 mol) of 1,6-hexylene diamine, 30 ml. of triethylamine, 45 ml. of dioxane and 30 ml. of water, at 10°–20° C., there is added 15 g. (0.038 mol) of IX. Stirring is continued for an additional 2 hours and the product mixture then is poured into 96 ml. of 6% aqueous sodium hydroxide. The aqueous mixture is washed with heptane, then extracted with methylene chloride. Concentrations of the methylene chloride extract yields 6 g. of a solid (X) melting at 98°–110° C.

The efficacy of the compounds of this invention as stabilizers against deterioration of polymers caused by ultraviolet light is shown by data obtained from tests carried out in a Fade-Ometer and Weather-Ometer. Test samples are prepared by extrusion from a Brabender extruder having a ¾-inch screw diameter. A sheet die is used which can be adjusted to produce a film 0.01 inch thick and 2 inches wide. The extruder is heated so that the temperature of the extruded film is about 500° F. as it leaves the die. The extruded material is pulled by a set of chrome rolls which are heated at about 50° C. and which polish the film and assure its uniform thickness. Care is taken not to pull the film too fast as it leaves the extruder so that the polymer remains unoriented. The extrusion of polypropylene under these conditions produces an extrudate having a tensile strength of about 5000 psi.

The Fade-Ometer is an enclosed box containing xenon lamps, the light from which simulates the ultraviolet radiation from the sun. The Weather-Ometer is a variation of the above wherein water is sprayed on the test samples, so as to simulate rain, for 20 minutes of each hour. The test samples are suspended in this environment by means of metal clamps and removed at periodic intervals for testing as regards deterioration of physical properties, i.e., tensile strength.

Three test samples are tested each time and the average of these three is taken as the tensile strength. They are pulled at a rate of 10 inches per minute on an Instron, which records the stretch or elongation of the sample and the force required to produce that elongation. When the sample yields and again when it breaks, the force and elongation are recorded. The force (in pounds) is divided by the cross-sectional area (in square inches) to give the tensile strength.

The product of Example 2 is subjected to such testing at periodic intervals after exposure to ultraviolet light in the Fade-Ometer as above. The formulation tested consisted of 100 parts of polypropylene containing 0.05 part of calcium stearate, 0.1 part of Irganox 1076 (octadecyl 3-(3', 5',-ditertiarybutyl-4'-hydroxyphenyl)propionate), and 0.5 part of the product of Example 2. The results are shown in Table I.

TABLE I

| | Hours of Exposure | Tensile Strength (lbs./sq. in.) |
|---|---|---|
| | 0 | 4478 |
| | 1000 | 4666 |
| Product of | 1500 | 3876 |
| Example 2 | 2000 | 4839 |
| | 3000 | 5057 |
| | 5000 | 3945 |

Similar test data is set out in Table II. It shows the retention of tensile strength of test samples prepared as above, upon exposure to ultraviolet light in a Weather-Ometer. The test samples in each case contained 100 parts of polypropylene, 0.05 part of calcium stearate, 0.1 part of Irganox 1076 and 0.5 part of the products of Examples 4 and 6.

TABLE II

| | Hours of Exposure | Tensile Strength (lbs./sq. in.) |
|---|---|---|
| | 0 | 5069 |
| Product of | 2000 | 5441 |
| Example 4 | 3500 | 4726 |
| | 5000 | 694 |
| | 0 | 4896 |
| | 2000 | 5381 |
| Product of | 3500 | 4554 |
| Example 6 | 4300 | 703 |
| | 4856 | 200 |

I claim:
1. A polymer composition stabilized against deterioration due to ultraviolet light and heat comprising a polyolefin and a minor proportion, sufficient to provide such stabilization, of a five-membered nitrogen ring compound having the structure AOCOR, ACOOR or ACONHR' where A is a 2,2,5,5-tetraalkyl pyrrolidine or pyrroline wherein the alkyl groups are lower alkyl, R is alkyl, alkOCOA or alkCOOA where alk is an alkylene residue of a dicarboxylic or dihydroxy compound, and R' is alkyl or alkNHCOA; or a salt thereof.
2. The polymer composition of claim 1 wherein the polyolefin is polypropylene.
3. The polymer composition of claim 1 wherein A is a 2,2,5,5-tetramethyl pyrrolidine.
4. The polymer composition of claim 1 wherein A is a 2,2,5,5-tetramethyl pyrroline.
5. The polymer composition of claim 1 wherein the five-membered nitrogen ring compound is AOCOalkCOOA.
6. The polymer composition of claim 1 wherein the five-membered nitrogen ring compound is ACONHR'.
7. The polymer composition of claim 5 wherein A is 2,2,5,5-tetraalkyl pyrrolidine.
8. The polymer composition of claim 5 wherein A is a 2,2,5,5-tetraalkyl pyrroline.
9. The polymer composition of claim 6 wherein R' is alkyl.
10. The polymer composition of claim 1 characterized further in that it also contains a polyvalent metal salt of a fatty acid.
11. The polymer composition of claim 1 characterized further in that it also contains a phenolic antioxidant.

* * * * *